(12) United States Patent
Grady et al.

(10) Patent No.: US 12,131,817 B2
(45) Date of Patent: *Oct. 29, 2024

(54) SYSTEMS AND METHODS FOR PROCESSING DIGITAL IMAGES FOR RADIATION THERAPY

(71) Applicant: PAIGE.AI, Inc., New York, NY (US)

(72) Inventors: Leo Grady, Darien, CT (US); Christopher Kanan, Pittsford, NY (US); Jorge S. Reis-Filho, New York, NY (US)

(73) Assignee: Paige.AI, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,907

(22) Filed: Oct. 12, 2022

(65) Prior Publication Data

US 2023/0114147 A1 Apr. 13, 2023

Related U.S. Application Data

(63) Continuation of application No. 17/493,917, filed on Oct. 5, 2021, now Pat. No. 11,501,869, which is a (Continued)

(51) Int. Cl.
*G16H 20/40* (2018.01)
*A61N 5/10* (2006.01)
(Continued)

(52) U.S. Cl.
CPC ............ *G16H 20/40* (2018.01); *A61N 5/103* (2013.01); *G06N 20/00* (2019.01); *G06T 7/0012* (2013.01);
(Continued)

(58) Field of Classification Search
None
See application file for complete search history.

(56) References Cited

U.S. PATENT DOCUMENTS

| 2006/0224539 A1 | 10/2006 | Zhang et al. |
| 2011/0060766 A1* | 3/2011 | Ehlke ............... G16H 30/00 715/810 |

(Continued)

OTHER PUBLICATIONS

Quantitative analysis of breast cancer diagnosis using a probabilistic modelling approach Author links open overlay panelShuo Liu a 1, Jinshu Zeng b 1, Huizhou Gong c, Hongqin Yang d, Jia Zhai e, Yi Cao f, Junxiu Liu g, Yuling Luo h, Yuhua Li i, Liam Maguire g, Xuemei Ding (Year: 2017).*

(Continued)

*Primary Examiner* — Nancy Bitar
(74) *Attorney, Agent, or Firm* — Bookoff McAndrews, PLLC

(57) ABSTRACT

Systems and methods are disclosed for predicting a resistance index associated with a tumor and surrounding tissue, comprising receiving one or more digital images of a pathology specimen, receiving additional information about a patient and/or a disease associated with the pathology specimen, determining at least one target region of the one or more digital images for analysis and removing a non-relevant region of the one or more digital images, applying a machine learning system to the one or more digital images to determine a resistance index for the target region of the one or more digital images, the machine learning system having been trained using a plurality of training images to predict the resistance index for the target region using a plurality of images of pathology specimens, and outputting the resistance index corresponding to the target region.

19 Claims, 6 Drawing Sheets

Related U.S. Application Data continuation of application No. 17/486,371, filed on Sep. 27, 2021, now Pat. No. 11,482,317.

(60) Provisional application No. 63/091,378, filed on Oct. 14, 2020.

(51) Int. Cl.
*G06N 20/00* (2019.01)
*G06T 7/00* (2017.01)
*G06V 10/25* (2022.01)
*G16H 50/30* (2018.01)

(52) U.S. Cl.
CPC ............. *G06V 10/25* (2022.01); *G16H 50/30* (2018.01); *G06T 2207/20081* (2013.01); *G06T 2207/30024* (2013.01); *G06T 2207/30096* (2013.01)

(56) References Cited

U.S. PATENT DOCUMENTS

| | | | |
|---|---|---|---|
| 2015/0169982 A1* | 6/2015 | Perry | G06V 10/462 |
| | | | 382/195 |
| 2016/0232425 A1* | 8/2016 | Huang | G06T 7/40 |
| 2017/0071479 A1 | 3/2017 | Kano et al. | |
| 2019/0228844 A1 | 7/2019 | Nakamura et al. | |
| 2020/0069973 A1 | 3/2020 | Lou et al. | |
| 2020/0160032 A1* | 5/2020 | Allen | G06T 7/0012 |
| 2021/0166785 A1* | 6/2021 | Yip | G06T 7/0012 |

OTHER PUBLICATIONS

Asifullah Khan et al: "A Survey of the Recent Architectures of Deep Convolutional Neural Networks", arxiv.org, Cornell University Library, 201 Olin Library Cornell University Ithaca, NY 14853, Jan. 18, 2019 (Jan. 18, 2019), XP081663048, DOI: 10.1007/S10462-020-09825-6.

Liu Shuo et al: "Quantitative analysis of breast cancer diagnosis using a probabilistic modelling approach", Computers in Biology and Medicine, New York, NY, US, vol. 92, Nov. 21, 2017 (Nov. 21, 2017), pp. 168-175, XP085333687, ISSN: 0010-4825, DOI: 10.1016/J.COMPBIOMED.2017.11.014.

Zhao Hai-Na et al: "Partially cystic thyroid cancer on conventional and elastographic ultrasound: a retrospective study and a machine learning assisted system", Annals of Translational Medicine, vol. 8, No. 7, Apr. 1, 2020 (Apr. 1, 2020), pp. 495-495, XP055876807, us ISSN: 2305-5839, DOI: 10.21037/atm.2020. 03.211 Retrieved from the Internet: URL:https://www.ncbi.nlm.nih.gov/pmc/articles/PMC7210215/pdf/atm-08-07-495.pdf.

\* cited by examiner

SYSTEMS AND METHODS FOR PROCESSING DIGITAL IMAGES FOR RADIATION THERAPY

RELATED APPLICATION(S)

This application is a continuation of and claims the benefit of priority to U.S. application Ser. No. 17/493,917, filed Oct. 5, 2021, which is a continuation of and claims the benefit of priority to U.S. application Ser. No. 17/486,371, filed Sep. 27, 2021, which claims priority to U.S. Provisional Application No. 63/091,378, filed Oct. 14, 2020, the entireties of which are incorporated herein by reference.

FIELD OF THE DISCLOSURE

Various embodiments of the present disclosure pertain generally to radiation therapy. More specifically, particular embodiments of the present disclosure relate to systems and methods for processing images for radiation therapy planning for a patient.

BACKGROUND

Radiation therapy (RT) is a critical component of the cancer therapy pipeline. Albeit curative in a large proportion of patients with early stage cancer, when delivered at standard doses RT can have acute side effects and importantly, chronic morbidity. Despite its efficacy, there are no clinically approved biomarkers to tailor radiation therapy approaches to individual patients. Furthermore, there are subsets of cancer patients who derive minimal benefit from standard radiation therapy and could either benefit from modified schedules of radiation-therapy, chemoradiation approaches, or forgoing radiotherapy. This disclosure describes a system to examine a patient's tumor and surrounding tissue in a histology section to help guide the delivery of radiation therapy to individual cancer patients, based on an assessment of the intrinsic tumor sensitivity to radiation, the tumor microenvironment and/or the likely radiotherapy-induced toxicity in surrounding tissues.

The foregoing general description and the following detailed description are exemplary and explanatory only and are not restrictive of this disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing images for radiation therapy planning for a patient.

A method for predicting a resistance index associated with a tumor and surrounding tissue, the method comprising receiving one or more digital images of a pathology specimen, receiving additional information about a patient and/or a disease associated with the pathology specimen, determining at least one target region of the one or more digital images for analysis and removing a non-relevant region of the one or more digital images, applying a machine learning system to the one or more digital images to determine a resistance index for the target region of the one or more digital images, the machine learning system having been trained using a plurality of training images to predict the resistance index for the target region using a plurality of images of pathology specimens, and outputting the resistance index corresponding to the target region.

A system for predicting a resistance index associated with a tumor and surrounding tissue includes a memory storing instructions; and at least one processor executing the instructions to perform a process including receiving one or more digital images of a pathology specimen, receiving additional information about a patient and/or a disease associated with the pathology specimen, determining at least one target region of the one or more digital images for analysis and removing a non-relevant region of the one or more digital images, applying a machine learning system to the one or more digital images to determine a resistance index for the target region of the one or more digital images, the machine learning system having been trained using a plurality of training images to predict the resistance index for the target region using a plurality of images of pathology specimens, and outputting the resistance index corresponding to the target region.

A non-transitory computer-readable medium storing instructions that, when executed by a processor, cause the processor to perform a method for predicting a resistance index associated with a tumor and surrounding tissue includes a memory storing instructions; and at least one processor executing the instructions to perform a process including receiving one or more digital images of a pathology specimen, receiving additional information about a patient and/or a disease associated with the pathology specimen, determining at least one target region of the one or more digital images for analysis and removing a non-relevant region of the one or more digital images, applying a machine learning system to the one or more digital images to determine a resistance index for the target region of the one or more digital images, the machine learning system having been trained using a plurality of training images to predict the resistance index for the target region using a plurality of images of pathology specimens, and outputting the resistance index corresponding to the target region.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
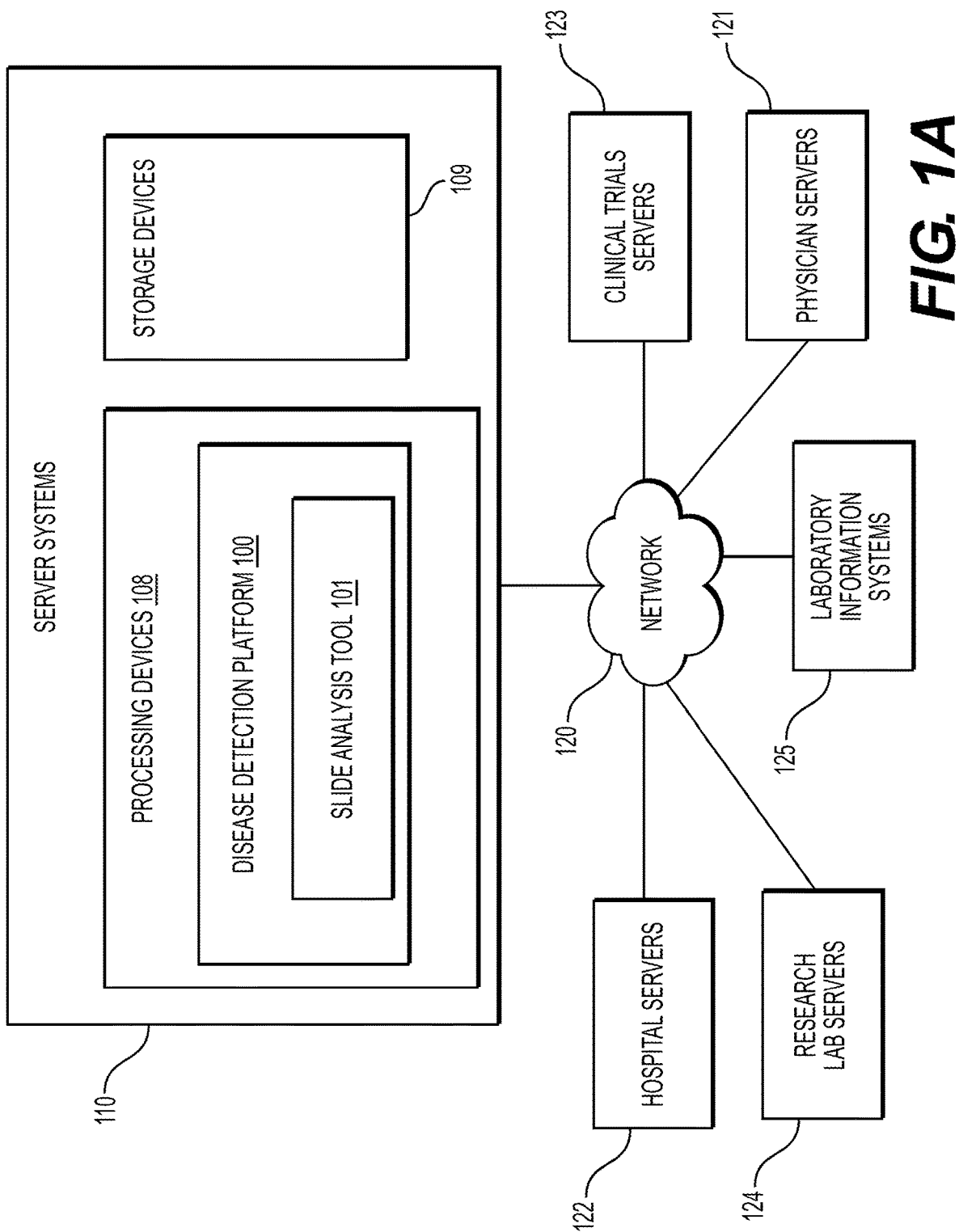
FIG. 1A illustrates an exemplary block diagram of a system and network for determining a resistance index of a target region of one or more digital images, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that these steps must be performed in the order presented but may instead by performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases, as well as the causes and effects of disease. More specifically, pathology refers to performing tests and analysis that are used to diagnose diseases. For example, tissue samples an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) that may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The present disclosure presents a method of using AI to detect and predict biomarkers and genomic panel features. In particular, the present disclosure describes various exemplary user interfaces available in the workflow, as well as AI tools that may be integrated into the workflow to expedite and improve a pathologist's work.

For example, computers may be used to analyze an image of a tissue sample to quickly identify whether additional information may be needed about a particular tissue sample, and/or to highlight to a pathologist an area in which he or she should look more closely. Thus, the process of obtaining additional stained slides and tests may be done automatically before being reviewed by a pathologist. When paired with automatic slide segmenting and staining machines, this may provide a fully automated slide preparation pipeline. This automation has, at least, the benefits of (1) minimizing an amount of time wasted by a pathologist determining a slide to be insufficient to make a diagnosis, (2) minimizing the (average total) time from specimen acquisition to diagnosis by avoiding the additional time between when additional tests are ordered and when they are produced, (3) reducing the amount of time per recut and the amount of material wasted by allowing recuts to be done while tissue blocks (e.g., pathology specimens) are in a cutting desk, (4) reducing the amount of tissue material wasted/discarded during slide preparation, (5) reducing the cost of slide preparation by partially or fully automating the procedure, (6) allowing automatic customized cutting and staining of slides that would result in more representative/informative slides from samples, (7) allowing higher volumes of slides to be generated per tissue block, contributing to more informed/precise diagnoses by reducing the overhead of requesting additional testing for a pathologist, and/or (8) identifying or verifying correct properties (e.g., pertaining to a specimen type) of a digital pathology image, etc.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

As described above, computational pathology processes, and devices of the present disclosure, may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

The present disclosure is directed to systems and methods for determining a resistance index for a tumor. One embodiment of the present disclosure may include a system trained to identify various properties of a digital pathology image, based on datasets of prior digital pathology images. The trained system may provide a resistance index for a specimen shown in a digital pathology image. The resistance index may help to provide treatment or diagnosis prediction(s) for a patient associated with the specimen.

FIG. 1A illustrates an exemplary block diagram of a system and network for determining a resistance index of a target region of one or more digital images, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a slide analysis tool 101 for determining specimen property or image property information pertaining to digital pathology image(s), and using machine learning to classify a specimen, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices 108 for processing images and data stored in the one or more storage devices 109. Server systems 110 may further include one or more machine learning tool(s) or capabilities. For example, the processing devices 108 may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a laboratory information systems 125. However, the correct tissue classification information is not always paired with the image content. Additionally, even if an LIS is used to access the specimen type for a digital pathology image, this label may be incorrect due to the fact that many components of an LIS may be manually inputted, leaving a large margin for error. According to an exemplary embodiment of the present disclosure, a specimen type may be identified without needing to access the laboratory information systems 125, or may be identified to possibly correct laboratory information systems 125. For example, a third party may be given anonymized access to the image content without the corresponding specimen type label stored in the LIS. Additionally, access to LIS content may be limited due to its sensitive content.

Figure 1B:
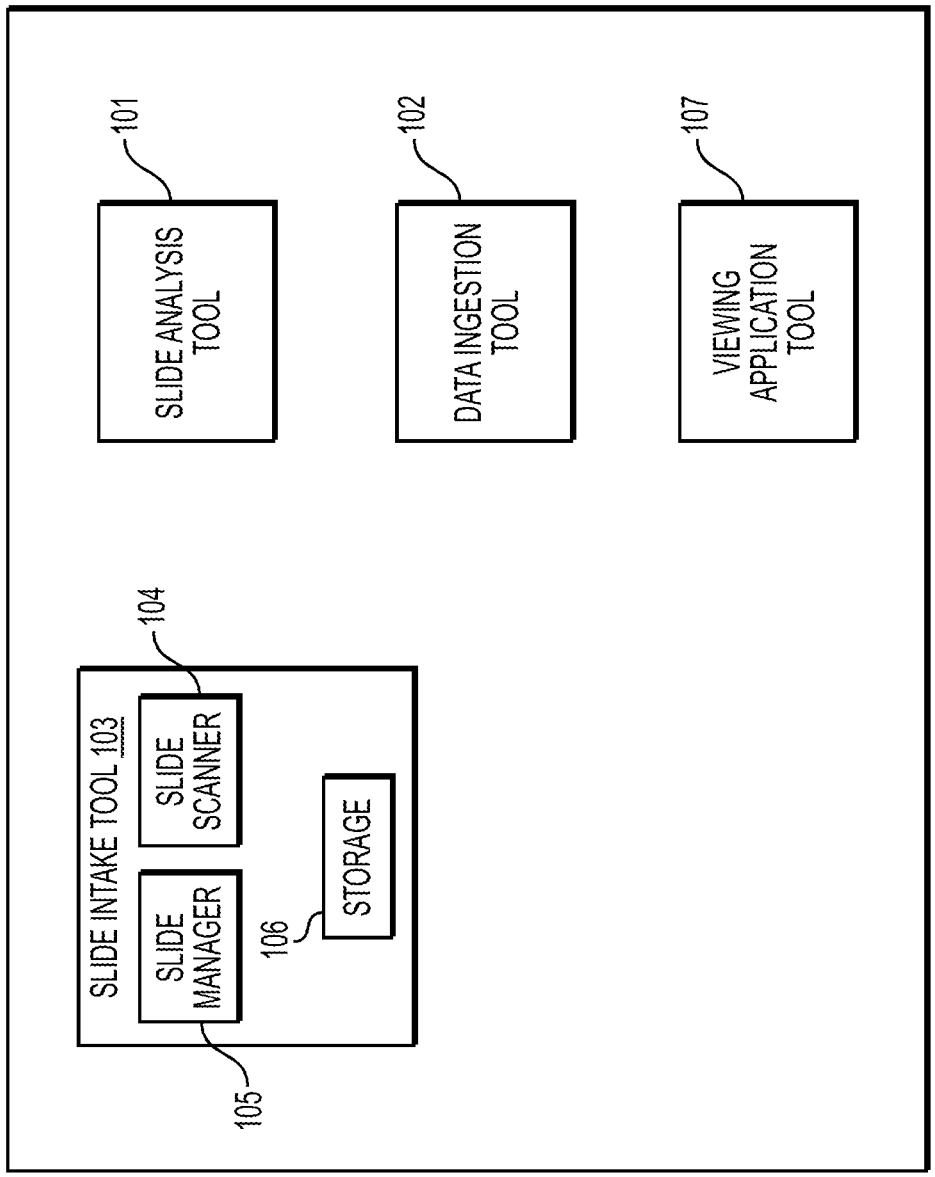
FIG. 1B illustrates an exemplary block diagram of a disease detection platform, according to an exemplary embodiment of the present disclosure.

FIG. 1B illustrates an exemplary block diagram of a disease detection platform 100, according to one embodiment. For example, the disease detection platform 100 may include a slide analysis tool 101, a data ingestion tool 102, a slide intake tool 103, a slide scanner 104, a slide manager 105, a storage 106, and a viewing application tool 107.

The slide analysis tool 101, as described below, refers to a process and system for determining specimen property or image property pertaining to digital pathology image(s), and using machine learning to determine a resistance index, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images into digitized pathology images and store the digitized images in storage 106.

The viewing application tool 107 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information servers 125 over the electronic network 120. Further, server systems 110 may include storage devices for storing images and data received from at least one of the slide analysis tool 101, the data ingestion tool 102, the slide intake tool 103, the slide scanner 104, the slide manager 105, and viewing application tool 107. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the systems and methods of the present disclosure) may be performed on a local processing device such as a laptop.

Any of the above devices, tools and modules may be located on a device that may be connected to an electronic network such as the Internet or a cloud service provider, through one or more computers, servers and/or handheld mobile devices.

Figure 1C:
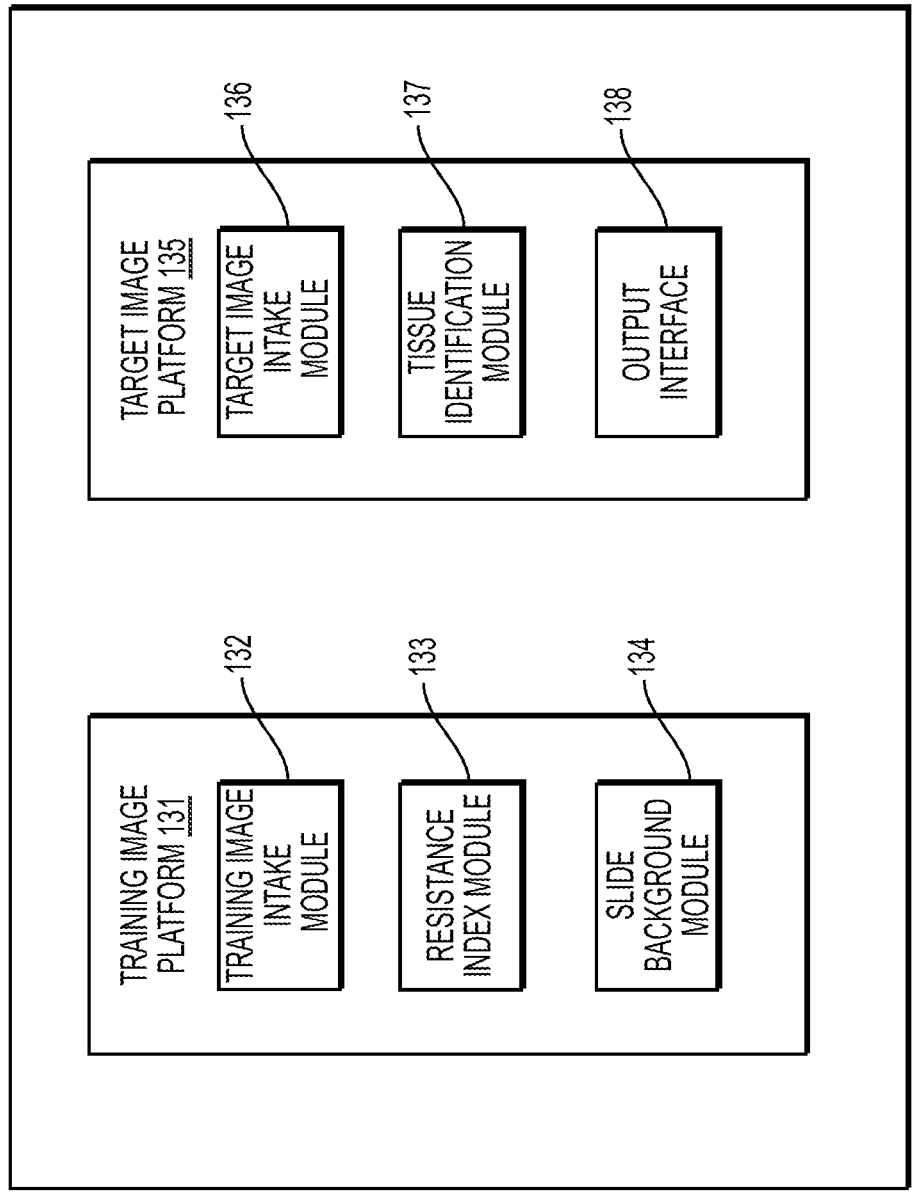
FIG. 1C illustrates an exemplary block diagram of a slide analysis tool, according to an exemplary embodiment of the present disclosure.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a training resistance index module 133, and a slide background module 134.

The training image platform 131, according to one embodiment, may create or receive training images that are used to train a machine learning model to effectively process, analyze, and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., artificial objects or obstructions generated in graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training images corresponding to either or both images of a human tissue and images that are graphically rendered. For example, the training images may be received from any one or any combination of the server systems 110, physician servers 121, hospital servers 122, clinical trial servers 123, research lab servers 124, and/or laboratory information systems 125. This dataset of images may be kept on a digital storage device. The training resistance index module 133 may detect a resistance index for each image, based on the received digital image(s) and received data. The slide background module 134 may predict a background within the image, based on the received digital image(s) and received data.

According to one embodiment, the target image platform 135 may include a target image intake module 136, a tissue identification module 137, and an output interface 138. The target image platform 135 may receive a target image and apply the machine learning model to the received target image to determine a resistance index. For example, the target image may be received from any one or any combination of server systems 110, physician servers 121, hospital servers 122, clinical trial servers 123, research lab servers 124 and/or laboratory information systems 125. The target image intake module 136 may receive a target image corresponding to a target specimen. The tissue identification module 137 may apply the machine learning model to the target image to detect a target region for analysis. For example, the tissue identification module 137 may apply the machine learning model to the target image to determine what regions are best suited for analysis.

The output interface 138 may be used to output information about the target image and the target specimen. The information may be output to a screen, a monitor, a storage device, a web browser or any other suitable output.

Figure 2A:
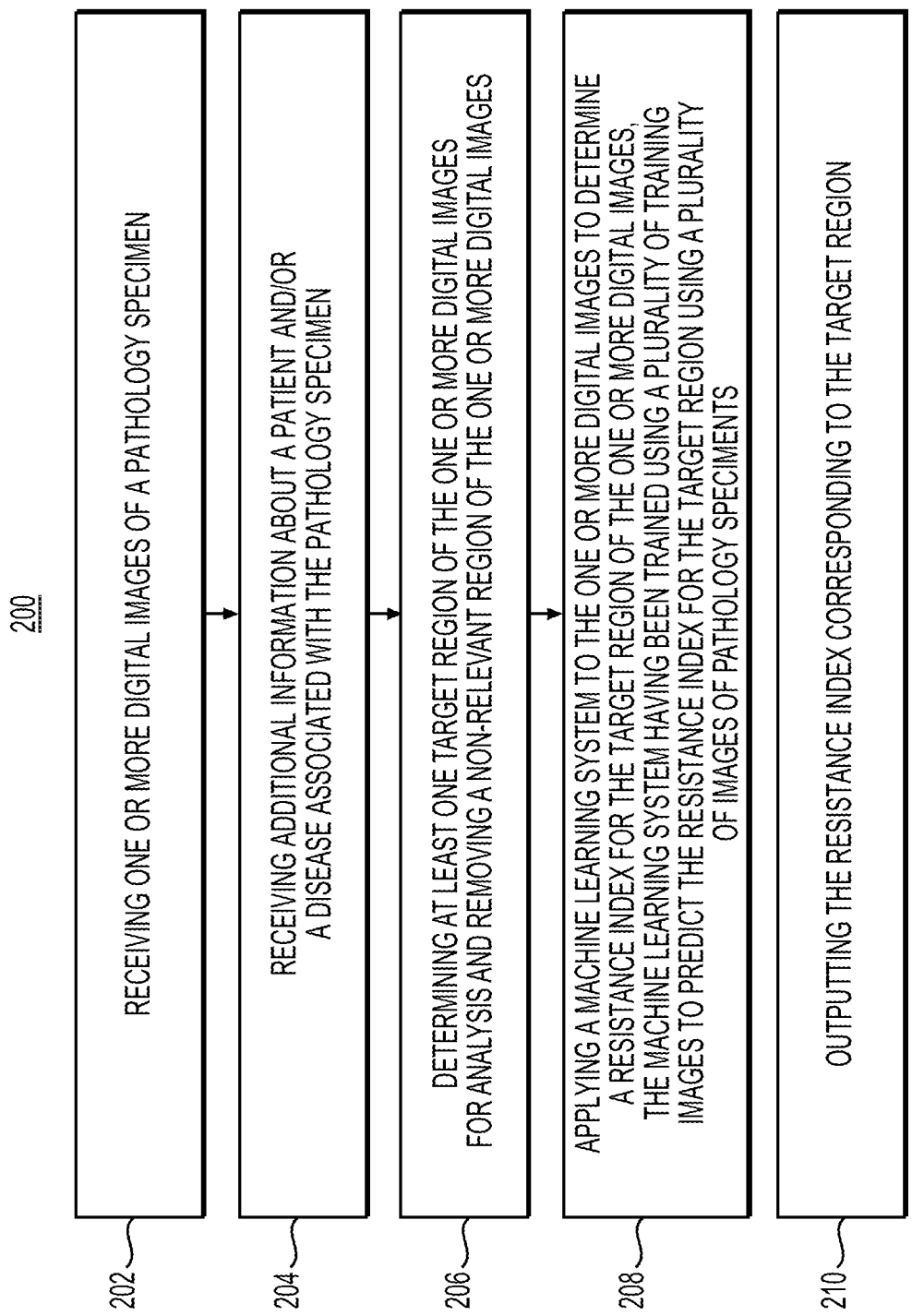
FIG. 2A is a flowchart illustrating an exemplary method for determining a resistance index of a target region, according to techniques presented herein.

FIG. 2A is a flowchart illustrating an exemplary method of determining a resistance index for a target region, using AI, according to an exemplary embodiment of the present disclosure. For example, an exemplary method 200 (e.g., steps 202-210) may be performed by the slide analysis tool 101 automatically or in response to a request from a user (e.g., physician, pathologist, etc.)

According to one embodiment, the exemplary method 200 for determining a resistance index of a pathology specimen may include one or more of the following steps, which may be optional and may be performed in any order. In step 202, the method may include receiving one or more images of a pathology specimen (e.g., histology, cytology, etc.) for storage at a digital storage device (e.g., hard drive, network drive, cloud storage, RAM, etc.). The pathology slides may be unstained or stained with one or more stains (e.g., H&E, IHC, FISH, CISH, special stains, etc.).

In step 204, the method may include receiving additional information about a patient and/or a disease associated with the pathology specimen. This additional patient information may include, but is not necessarily limited to, patient demographics, prior medical history, additional test results, radiology imaging, genomic test results, molecular test results, historical pathology specimen images, information about the specimen (e.g., location of specimen sample, position in block, etc.), etc., for storage at a digital storage device (e.g., hard drive, network drive, cloud storage, RAM, etc.).

In step 206, the method may include identifying a target region of the one or more digital images for analysis and removing a non-relevant region of the one or more digital images. Examples of a target region could be a tumor, a tumor with surrounding margin or other biological, pathological structures or tissue regions. The target region may be automatically determined (e.g., via an automatic tumor detection system) or manually determined (e.g., via a user interface allowing the marking of the target region). If no target region is specified, then the entire one or more slides is considered the target region. If the one or more target regions is a subset of the one or more slides, one or more additional target regions may be defined comprising any remaining region of the one or more slides that was not specified as belonging to a target region.

In step 208, the method may include applying a machine learning system to the one or more digital images to determine a resistance index for one or more target regions on the one or more digital images, the machine learning system having been trained using a plurality of training images and/or additional information to predict the resistance for the one or more target regions. The resistance of the one or more target regions and remaining area may be quantified by a resistance index and/or a binary treatment suitability assessment (hereafter referred to as simply a resistance index). The resistance indices may be different for the one or more target regions.

In step 210, the method may include outputting the resistance index corresponding to one or more target areas to an electronic storage device (e.g., hard drive, RAM, network drive, cloud, etc.) and/or display the resistance index to a user display (e.g., a monitor, touchscreen, etc.) and/or an output document (e.g., PDF, printout, etc.).

Figure 2B:
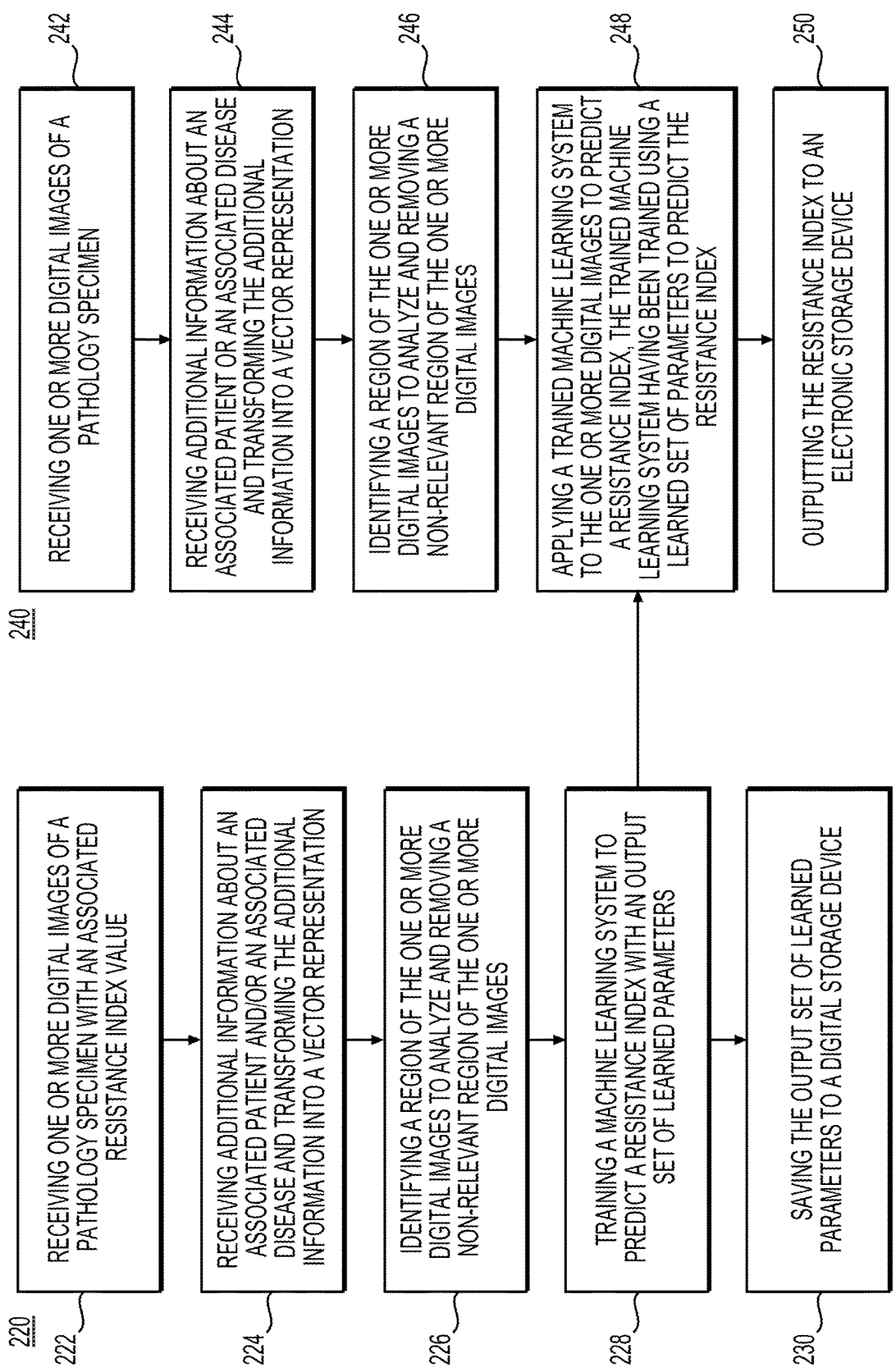
FIG. 2B is a flowchart illustrating an exemplary method for training and using a machine learning system to predict a resistance index and set of learned parameters for a patient, according to techniques presented herein.

FIG. 2B is a flowchart illustrating an exemplary method for determining a resistance index of a target region, according to techniques presented herein. The resistance index prediction system may be created using machine learning to fit parameters of a model using training data (e.g., slides and patient information paired with resistance index information). After training, the system can be used with individual patients to predict their resistance index. Exemplary method 220 (e.g., steps 222-230) and exemplary method 240 (e.g., steps 242-250) for training the system and using the trained system are described below. All steps may be optional and may be used in any order.

In step 222, the method may include receiving one or more digital images of a pathology specimen (e.g., histology, cytology, etc.) with an associated resistance index value at a digital storage device (e.g., hard drive, network drive, cloud storage, RAM, etc.). The pathology slides may be unstained or stained with one or more stains (e.g., H&E, IHC, FISH, CISH, special stains, etc.). For each slide, the resistance index value corresponding to the benefit of the radiation therapy, which can be a continuous (real) number (e.g., higher values indicate radiation being more effective) or binary (e.g., 1 indicates radiation being more effective), is received. The resistance indices may be produced from studies on patients and then recording the degree of benefit patients derived from the radiation therapy.

In step 224, the method may include receiving additional information about an associated patient and/or an associated disease and transforming the additional information into a vector representation. This additional patient information may include, but is not necessarily limited to, patient demographics, prior medical history, additional test results, radiology imaging, genomic test results, molecular test results, historical pathology specimen images, information about the specimen (e.g., location of specimen sample, position in block), etc., into a digital storage device (e.g., hard drive, network drive, cloud storage, RAM, etc.). The vector representation may include a portion of the vector corresponding to binary information regarding demographics, a portion may be devoted to positive/negative genomic test results, etc.

In step 226, the method may include identifying a target region of the one or more digital images to analyze and removing non-relevant regions of the digital image. Identifying the target regions may be done by use of an AI system or by manual annotation.

In step 228, the method may include training a machine learning system to predict a resistance index with an output set of learned parameters. For continuous resistance index values, the system may be trained with a regression loss (e.g., mean squared error loss, Huber loss, etc.) and for binary resistance index values it may be trained with a classification loss (e.g., hinge, log loss, etc.). If available, the vector of patient information may be integrated into the prediction by concatenating it into the representations within a neural network system, used to modulate the outputs by adopting a probabilistic approach, or by modulating the processing of the neural network (e.g., using conditional batch normalization). Machine learning systems that may be trained include, but are not limited to:
   a. Convolutional neural network (CNN) trained directly with the appropriate loss function.
   b. CNN with CoordConv layers with the appropriate loss function.
   c. Capsule network with the appropriate loss function.
   d. Transformer network with the appropriate loss function.
   e. Multiple instance learning with a CNN (for a binary resistance index value)
   f. Multiple instance regression with a CNN (for a continuous resistance index value), etc.

In step 230, the method may include saving the set of learned parameters from the resistance index to a digital storage device (e.g., hard drive, network drive, cloud storage, RAM, etc.).

Once the resistance index and set of learned parameters is obtained, method 240 may be used with individual patients to predict their resistance index after training. In step 242, the method may include receiving one or more digital images of a pathology specimen (e.g., histology, cytology, etc.) of a patient, which may be stored at a digital storage device (e.g., hard drive, network drive, cloud storage, RAM, etc.). The pathology slides may be unstained or stained with one or more stains (e.g., H&E, IHC, FISH, CISH, special stains, etc.).

In step 244, the method may include receiving additional information about an associated patient or an associated disease and transforming the additional information into a vector representation. This additional information may include, but is not limited to, patient demographics, prior medical history, additional test results, radiology imaging, genomic test results, molecular test results, historical pathology specimen images, information about the specimen (e.g., location of specimen sample, position in block, etc.) etc. into a digital storage device (e.g., hard drive, network drive, cloud storage, RAM, etc.). Transforming the additional information into a vector representation may include a portion of the vector may correspond to binary information regarding demographics, a portion can be devoted to positive/negative genomic test results, etc.

In step 246, the method may include identifying a target region of the one or more digital images to analyze and removing a non-relevant region. Identification may be accomplished by using an AI system or manual annotation.

In step 248, the method may include applying a trained machine learning system to the one or more digital images to predict a resistance index, the trained machine learning system having been trained using a learned set of parameters to predict a resistance index, as described in method 220.

In step 250, the method may include outputting the resistance index to an electronic storage device, display, file, etc. The method may optionally also include using a visual indicator to alert the user to the resistance index predicted by the trained system.

Figure 3:
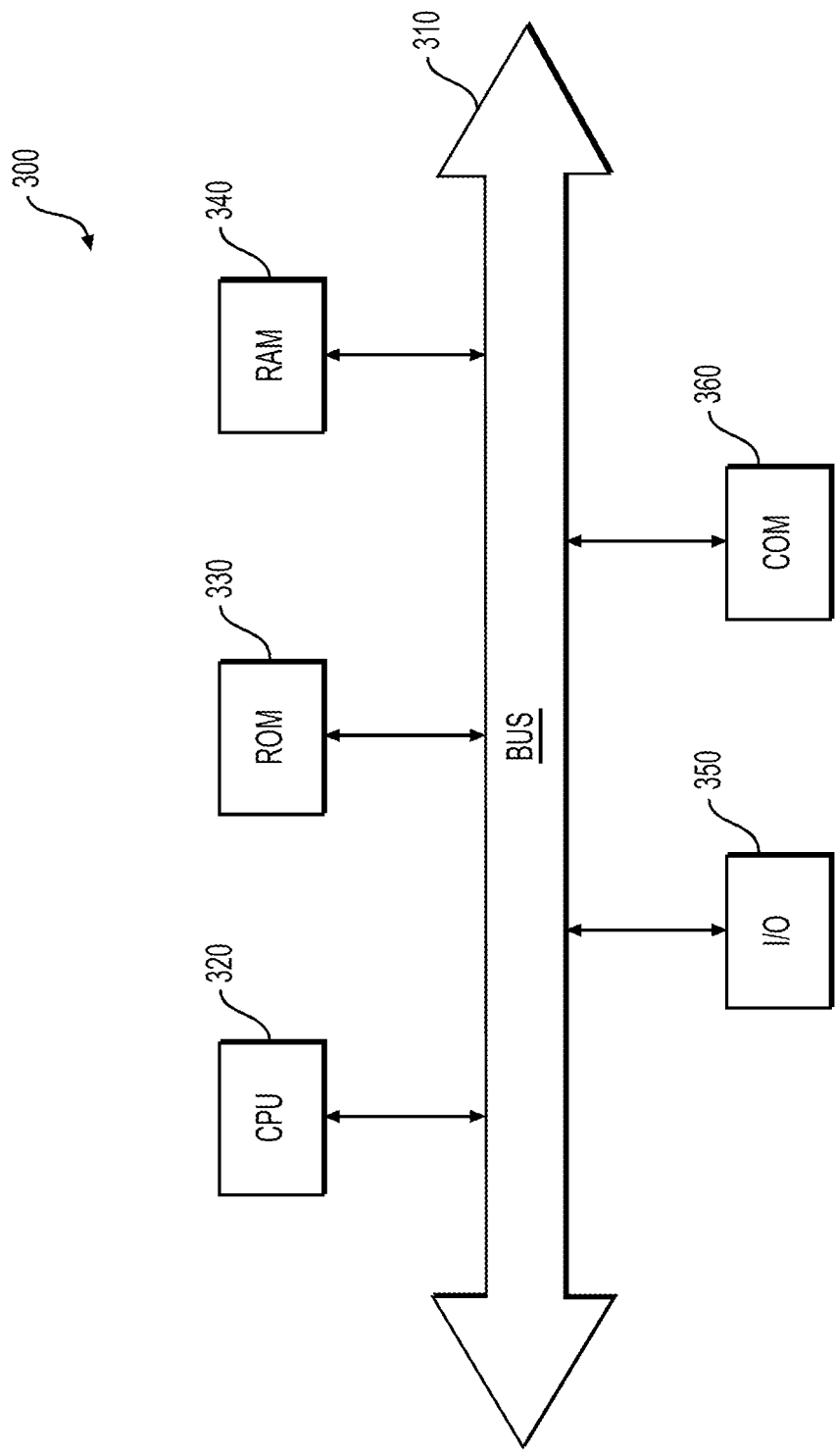
FIG. 3 illustrates an example system that may execute techniques presented herein.

As shown in FIG. 3, device 300 may include a central processing unit (CPU) 320. CPU 320 may be any type of processor device, including, for example, any type of special purpose or a general-purpose microprocessor device. As will be appreciated by persons skilled in the relevant art, CPU 320 may also be a single processor in a multi-core/multi-processor system, such system operating alone, or in a cluster of computing devices operating in a cluster or server farm. CPU 320 may be connected to a data communication infrastructure 310, for example a bus, message queue, network, or multi-core message-passing scheme.

Device 300 may also include a main memory 340, for example, random access memory (RAM), and also may include a secondary memory 330. Secondary memory 330, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, a magnetic tape, an optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 330 may include similar means for allowing computer programs or other instructions to be loaded into device 300. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 300.

Device 300 may also include a communications interface ("COM") 360. Communications interface 360 allows software and data to be transferred between device 300 and external devices. Communications interface 360 may include a modem, a network interface (such as an Ethernet card), a communications port, a PCMCIA slot and card, or the like. Software and data transferred via communications interface 360 may be in the form of signals, which may be electronic, electromagnetic, optical, or other signals capable of being received by communications interface 360. These signals may be provided to communications interface 360 via a communications path of device 300, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 300 may also include input and output ports 350 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and exemplar are to be considered exemplary only.

What is claimed is:

1. A computer-implemented method for predicting a benefit of radiation therapy, the method comprising: receiving one or more digital images of a pathology specimen; receiving additional information about a patient and/or a disease associated with the pathology specimen and transforming the additional information into a vector representation;
    identifying a target region of one or more digital images for analysis, the target region including at least a portion of a detected tumor and tissue surrounding the detected tumor;
    removing a non-relevant region of the one or more digital images;
    applying a machine learning system to the one or more digital images to predict a benefit of radiation therapy for the target region by integrating the vector representation into a neural network of the machine learning system, the machine learning system having been trained by processing a plurality of training images to predict the benefit of radiation therapy for the target region, wherein the predicted benefit of radiation therapy is based on an intrinsic sensitivity of the detected tumor to radiation and/or a probability of radiotherapy-induced toxicity in the tissue surrounding the detected tumor; and
    outputting the predicted benefit of radiation therapy corresponding to the target region to an electronic storage device.

2. The computer-implemented method of claim 1, further comprising alerting a user with a visual indicator when the benefit of radiation therapy is available.

3. The computer-implemented method of claim 1, further comprising:
    detecting one or more tumors in the received one or more digital images, wherein identifying the target region of the one or more digital images for analysis is done by using the machine learning system and is based on the detected one or more tumors;
    identifying an additional target region of the one or more digital images for analysis using the machine learning system and based on the detected one or more tumors, and
    applying the machine learning system to the one or more digital images to predict an additional benefit of radiation therapy for the additional target region.

4. The computer-implemented method of claim 1, wherein identifying the target region of the one or more digital images for analysis is done manually.

5. The computer-implemented method of claim 1, wherein the target region comprises an entire slide image of the one or more digital images.

6. The computer-implemented method of claim 1, wherein no target region is identified and an entire one or more digital slides is analyzed.

7. The computer-implemented method of claim 1, wherein using a plurality of training images to predict the benefit of radiation therapy comprises:
    receiving one or more digital images of a pathology specimen;
    receiving additional information about an associated patient or an associated disease and transforming the additional information into a vector representation;
    identifying a region of the one or more digital images to analyze and removing a non-relevant region;
    applying a trained machine learning system to the one or more digital images to predict the benefit of radiation therapy, the trained machine learning system having been trained using a learned set of parameters to predict the benefit of radiation therapy; and
    outputting the benefit of radiation therapy to an electronic storage device.

8. The computer-implemented method of claim 7, wherein using a learned set of parameters to predict the benefit of radiation therapy comprises:
    receiving one or more digital images of a pathology specimen with an associated benefit of radiation therapy value;
    receiving additional information about an associated patient and/or an associate disease and transforming the additional information into a vector representation;
    identifying a region of the one or more digital images to analyze and removing a non-relevant region of the one or more digital images;
    training a machine learning system to predict the benefit of radiation therapy with an input set of learned parameters; and
    saving an output set of learned parameters to a digital storage device.

9. The computer-implemented method of claim 8, wherein the associated benefit of radiation therapy value is:
- a continuous number, and training the machine learning system is done with a regression loss; or
- a binary number, and training the machine learning system is done with a classification loss.

10. The method of claim 1, wherein:
- the plurality of training images included a plurality of images of pathology specimens associated with a plurality of patients,
- the machine learning system was trained using additional information about the plurality of patients and/or one or more diseases associated with the plurality of patients, and
- wherein training the machine learning system using the plurality of training images includes transforming the additional information into a vector representation and integrating the vector representation into the prediction by:
  - concatenating the vector representation into representations within the neural network system to modulate outputs by adopting a probabilistic approach, or
  - modulating processing of the neural network system using conditional batch normalization.

11. The method of claim 1, wherein training the machine learning system includes:
- receiving the plurality of training images;
- receiving additional information;
- transforming the additional information into a vector representation; and
- concatenating the vector representation into representations within the neural network system to modulate outputs by adopting a probabilistic approach.

12. A system for predicting a benefit of radiation therapy, comprising:
- at least one memory storing instructions; and
- at least one processor configured to execute the instructions to perform operations comprising:
  - receiving one or more digital images of a pathology specimen;
  - receiving additional information about a patient and/or a disease associated with the pathology specimen and transforming the additional information into a vector representation;
  - identifying a target region of one or more digital images for analysis;
  - applying a machine learning system to the one or more digital images to predict a benefit of radiation therapy for the target region by integrating the vector representation into a neural network of the machine learning system, the machine learning system having been trained by processing a plurality of training images to predict the benefit of radiation therapy for the target region; and
  - outputting the predicted benefit of radiation therapy corresponding to the target region to an electronic storage device.

13. The system of claim 12, wherein the operations further comprise alerting a user with a visual indicator when the benefit of radiation therapy is available.

14. The system of claim 12, wherein identifying the target region of the one or more digital images for analysis is done by using a machine learning system.

15. The system of claim 12, wherein identifying the target region of the one or more digital images for analysis is done manually.

16. The system of claim 12, wherein the operations further comprise:
- removing a non-relevant region of the one or more digital images, the target region including at least a portion of a detected tumor and tissue surrounding the detected tumor, and
- wherein the benefit of radiation therapy is based on an intrinsic sensitivity of the detected tumor to radiation and/or a probability of radiotherapy-induced toxicity in the tissue surrounding the detected tumor.

17. The system of claim 12, wherein no target region is identified and an entire one or more digital slides is analyzed.

18. The system of claim 12, wherein using a plurality of training images to predict the benefit of radiation therapy comprises:
- receiving one or more digital images of a pathology specimen;
- receiving additional information about an associated patient or an associated disease and transforming the additional information into a vector representation;
- identifying a region of the one or more digital images to analyze and removing a non-relevant region;
- applying a trained machine learning system to the one or more digital images to predict the benefit of radiation therapy, the trained machine learning system having been trained using a learned set of parameters to predict the benefit of radiation therapy; and
- outputting the benefit of radiation therapy to an electronic storage device.

19. A non-transitory computer-readable medium storing instructions that, when executed by a processor, cause the processor to perform operations for predict a benefit of radiation therapy, the operations comprising: receiving one or more digital images of a pathology specimen; receiving additional information about a patient and/or a disease associated with the pathology specimen and transforming the additional information into a vector representation; identifying a target region of one or more digital images for analysis; the target region including at least a portion of a detected tumor and tissue surrounding the detected tumor;
- removing a non-relevant region of the one or more digital images;
- applying a machine learning system to the one or more digital images to predict a benefit of radiation therapy for the target region by integrating the vector representation into a neural network of the machine learning system, the machine learning system having been trained by processing a plurality of training images to predict the benefit of radiation therapy for the target region; wherein the predicted benefit of radiation therapy is based on an intrinsic sensitivity of the detected tumor to radiation and/or a probability of radiotherapy-induced toxicity in the tissue surrounding the detected tumor; and outputting the predicted benefit of radiation therapy corresponding to the target region to an electronic storage device.

* * * * *